United States Patent [19]

Muckenfuhs et al.

[11] Patent Number: 5,295,988
[45] Date of Patent: Mar. 22, 1994

[54] INDIVIDUALLY WRAPPED DISPOSABLE ABSORBENT ARTICLE WHICH BECOMES ELASTICIZED WHEN UNWRAPPED

[75] Inventors: Delmar R. Muckenfuhs, Middletown, Ohio; Kim M. Roy, Lynn, Mass.

[73] Assignee: The Procter & Gamble Company, Cincinnati, Ohio

[21] Appl. No.: 941,341

[22] Filed: Sep. 4, 1992

[51] Int. Cl.⁵ .................... A61F 13/15; A61F 13/20
[52] U.S. Cl. .................... 604/385.2; 604/358; 604/385.1; 604/386; 604/389; 604/390
[58] Field of Search .................... 206/440, 438–439, 206/441; 604/358, 385.1, 385.2, 386, 389, 390, 393; 602/57–58

[56] References Cited

U.S. PATENT DOCUMENTS

| | | | |
|---|---|---|---|
| 2,281,473 | 4/1942 | Brewer | 206/438 |
| 3,183,909 | 5/1965 | Roehr. | |
| 3,343,543 | 9/1967 | Glassman. | |
| 4,023,571 | 5/1977 | Comerford et al.. | |
| 4,081,301 | 3/1978 | Buell. | |
| 4,487,643 | 12/1984 | Ellett. | |
| 4,556,146 | 12/1985 | Swanson et al.. | |
| 4,585,607 | 4/1986 | Krackeler et al.. | |
| 4,598,528 | 7/1986 | McFarland et al.. | |
| 4,640,859 | 2/1987 | Hansen et al.. | |
| 4,668,230 | 5/1987 | Damico et al. | 604/385.2 |
| 4,743,245 | 5/1988 | Lassen et al. | 604/385.1 |
| 4,770,657 | 9/1988 | Ellis et al. | 604/385.2 |
| 4,772,282 | 9/1988 | Oakley. | |
| 4,848,572 | 7/1989 | Herrera. | |
| 4,886,513 | 12/1989 | Mason, Jr. et al.. | |
| 4,908,247 | 3/1990 | Baird et al.. | |
| 4,911,701 | 3/1990 | Mavinkurve. | |
| 4,944,735 | 7/1990 | Mokry | 604/385.2 |
| 5,129,893 | 7/1992 | Thoren. | |
| 5,133,477 | 7/1992 | Etheredge, III et al. | 206/441 |
| 5,181,563 | 1/1993 | Amaral. | |

*Primary Examiner*—Randall L. Green
*Assistant Examiner*—P. Zuttarelli
*Attorney, Agent, or Firm*—Kevin C. Johnson; E. Kelly Linman; Michael E. Hilton

[57] ABSTRACT

An article of manufacture is disclosed for absorbing liquids, particularly body fluids such as menses. The disclosed article is disposable and has a wrapper associated therewith. An elastic material is secured to the backsheet and is maintained in a substantially tensioned state until separation of the wrapper from the backsheet. Upon separation of the wrapper from the backsheet the tension in the elastic member is released causing the disposable absorbent article to form an upwardly cupped configuration to conform more closely to the wearer's body.

22 Claims, 9 Drawing Sheets

INDIVIDUALLY WRAPPED DISPOSABLE ABSORBENT ARTICLE WHICH BECOMES ELASTICIZED WHEN UNWRAPPED

FIELD OF THE INVENTION

The present invention pertains to individually wrapped disposable absorbent articles, and more particularly, to such individually wrapped disposable absorbent articles which restrain the elastic forces while wrapped and which free the elastic forces when unwrapped, allowing them to act on the absorbent article.

BACKGROUND OF THE INVENTION

All manner and variety of absorbent articles configured for the absorption of bodily fluids are, of course, well known. Current types of absorbent articles include sanitary napkins, pantiliners, diapers, and incontinent articles.

Several prior art structures have been developed to improve the overall fit of absorbent articles so that they more readily conform to the contours of the human body. By improving the fit of the absorbent article, it is expected that the performance of the absorbent article will also improve. In some prior art sanitary napkins elastic has been placed along the lateral edges of the sanitary napkin. The elastic is contained within the material comprising the absorbent article and therefore is not visible to the consumer. The elastic provides the sanitary napkin with an upwardly cupped shape improving the overall fit of the sanitary napkin to the body. However, there are numerous packaging, transport and storage problems associated with articles having an upwardly cupped shape.

Other prior art sanitary napkins are of a substantially planar configuration making them easier to package, transport, and store. However, these prior art sanitary napkins remain in their substantially planar configuration throughout their use. While being easier to package, transport and store, the substantially planar sanitary napkin does not readily conform to the contours of the human body. According, the substantially planar sanitary napkin provides an overall fit which is perceived as less than desirable by some users who prefer the upwardly cupped configuration.

Accordingly, it is desirable to produce an individually wrapped absorbent article, e.g., sanitary napkin, which can be packaged, transported, and stored in a substantially planar or flat configuration and yet conform substantially to the contours of the human body upon removal of the absorbent article from the package by the user.

SUMMARY OF THE INVENTION

The present invention provides an individually wrapped disposable absorbent article. The absorbent article includes an absorbent core which has a first surface and a second surface. A fluid permeable topsheet is secured in overlaying relation to the first surface of the absorbent core. A fluid impermeable backsheet is secured in overlaying relation to the second surface of the absorbent core. The exposed surface of the backsheet includes a layer of adhesive for securing the absorbent article to the user's undergarment. A wrapper covers the adhesive containing portion of the exposed surface of the backsheet. The wrapper is releasably affixed to the backsheet by virtue of the adhesive. The absorbent article is maintained in a substantially planar configuration while the wrapper is affixed to the backsheet. The absorbent article forms an upwardly cupped configuration when the wrapper is separated from the backsheet.

Preferably, an elastic material is secured to the exposed surface of the backsheet. A restraint material is releasably secured in fixed relation to the elastic material, thereby maintaining the elastic material in a substantially tensioned state until separation of the wrapper from the backsheet.

Preferably, the wrapper maintains the elastic material in a substantially tensioned state until separation of the wrapper from the backsheet. Preferably, stiffening members are secured to the inwardly oriented surface of the wrapper.

Preferably, an elastic material is secured to the inwardly oriented surface of the backsheet. The elastic material may also be secured to the absorbent core.

Preferably, an adhesive tab is secured to the exposed surface of the wrapper for maintaining the disposable absorbent article in a secured condition until opening. A release paper is positioned between the wrapper and the backsheet.

The present invention provides an individually wrapped disposable absorbent article which becomes elasticized when unwrapped. The absorbent article includes an absorbent pad which has a first surface and a second surface. A fluid permeable topsheet is secured in overlaying relation to the first surface of the absorbent pad. A fluid impermeable backsheet is secured in overlaying relation to the second surface of the absorbent pad. The exposed surface of the backsheet preferably includes a layer of adhesive for securing the absorbent article to the user's undergarment. A wrapper covers the adhesive containing portions of the exposed surface of the backsheet. The wrapper is releasably affixed to the backsheet by virtue of the adhesive. A tensioned elastic material is releasably secured in fixed relation to the wrapper and holds the elastic material in a substantially tensioned state. The elastic material is permanently secured to the exposed surface of the backsheet such that separation of the wrapper from the backsheet exposes the adhesive on the backsheet and releases the tension in the elastic member causing the disposable absorbent article to form an upwardly cupped configuration and to elastically shirr in the direction of tension release.

Preferably, a restraint material is releasably secured in fixed relation to the elastic material, thereby maintaining the elastic material in a substantially tensioned state until separation of the wrapper from the backsheet.

Preferably, stiffening members are secured to the inwardly oriented face of the wrapper.

In another embodiment, the present invention provides an individually wrapped disposable absorbent article which becomes elasticized when unwrapped. The absorbent article includes an absorbent pad which has a first surface and a second surface. A fluid permeable topsheet is secured in overlaying relation to the first surface of the absorbent pad. A fluid impermeable backsheet is secured in overlaying relation to the second surface of the absorbent pad. The exposed surface of the backsheet preferably includes a layer of adhesive. The pad includes a perimeter having longitudinal perimeter segments. A wrapper covers the adhesive containing portions of the exposed surface of the backsheet. The wrapper i s releasably affixed to the backsheet by virtue of the adhesive. An elastic material is permanently secured to the inwardly oriented surface of the backsheet. The wrapper maintains the elastic material in a substantially tensioned state until separation of the wrapper from the backsheet. Separation of the wrapper from the backsheet exposes the adhesive on the backsheet and releases the tension in the elastic member causing the disposable absorbent article to form an upwardly cupped configuration and to elastically shirr in the direction of tension release. The absorbent pad and the wrapper are preferably folded as a unit about at least two fold-axes and the longitudinal flap portions are frangably sealed.

Preferably, the individually wrapped disposable absorbent article includes a securement means on the exposed surface of the wrapper. The interior surface of the wrapper is preferably release coated.

BRIEF DESCRIPTION OF THE DRAWINGS

While the specification concludes with claims particularly pointing out and distinctly claiming the subject matter of the present invention, it is believed that the present invention will be better understood from the following description and drawings, in which like reference numerals identify identical elements and wherein;

DETAILED DESCRIPTION OF THE INVENTION

1. General Description of the Absorbent Article

As used herein, the term "absorbent article" refers to devices which absorb and contain body exudates, and, more specifically, refers to devices which are placed against or in proximity to the body of the wearer to absorb and contain the various exudates discharged from the body. The term "absorbent article" is intended to include diapers, catamenial pads, sanitary napkins, pantiliners, incontinent pads, and the like. The term "disposable" is used herein to describe absorbent articles which are not intended to be laundered or otherwise restored or reused as an absorbent article (i.e., they are intended to be discarded after a single use, and, preferably, to be composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
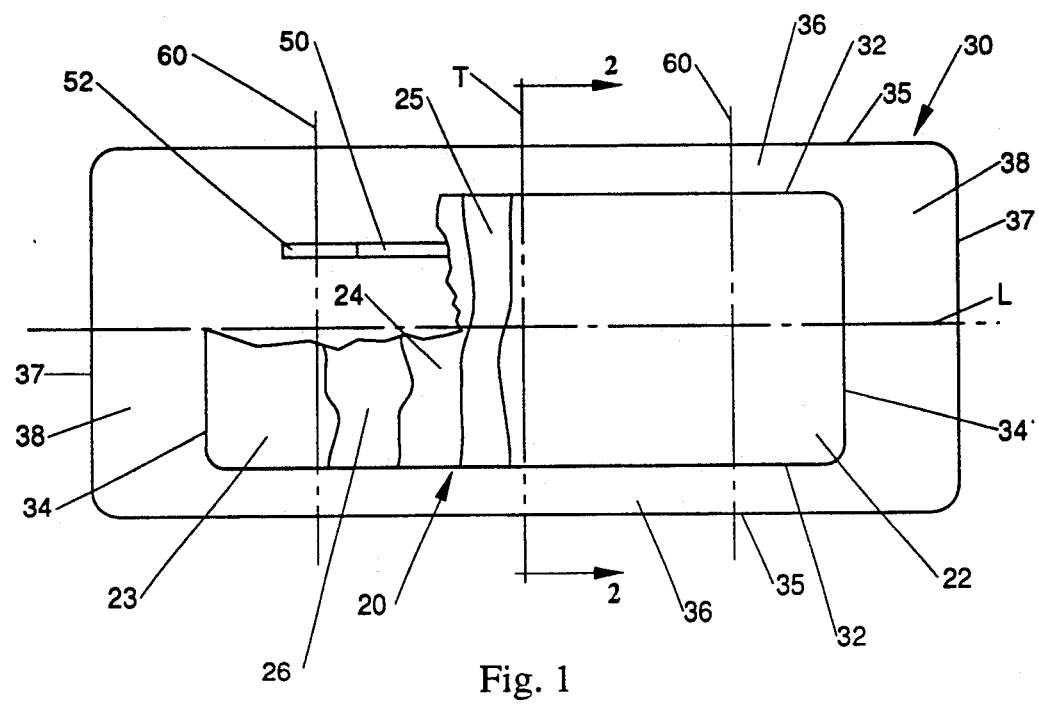
FIG. 1 is a top plan view of a preferred sanitary napkin of the present invention with portions cut-away to more clearly show the construction of the sanitary napkin.

A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

The sanitary napkin 20 has two surfaces, a body-contacting surface or "body surface" 20a and a garment surface 20b. The sanitary napkin 20 is shown in FIG. 1 as viewed from its body surface 20a. The body surface 20a is intended to be worn adjacent to the body of the wearer. The garment surface 20b of the sanitary napkin 20 (shown in FIG. 2) is on the opposite side and is intended to be placed adjacent to the wearer's undergarments when the sanitary napkin 20 is worn.

The sanitary napkin 20 has two centerlines, a longitudinal centerline "l" and a transverse centerline "t". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

FIG. 1 is a top plan view of the sanitary napkin 20 and a wrapper 30 of the present invention in its flat state with portions of the structure being cut-away to more clearly show the construction of the sanitary napkin 20 and with the portion of the sanitary napkin 20 which faces or contacts the wearer 20a, oriented towards the viewer. As shown in FIG. 1, the sanitary napkin 20 preferably comprises a liquid pervious topsheet 22, a liquid impervious backsheet 23 joined with the topsheet 22, and an absorbent core 24 positioned between the topsheet 22 and the backsheet 23.

The sanitary napkin 20 can also be provided with one or more additional layers or components. These include an acquisition layer (or the "secondary topsheet") 25 positioned generally between the topsheet 22 and the absorbent core 24. The sanitary napkin 20 also includes a nonwoven layer 26 positioned between the absorbent core 24 and the backsheet 23. The nonwoven layer 26 serves to keep the material of the absorbent core 24 from tearing (when the core is comprised of a cross-linked cellulose fibers) and the layers of the sanitary napkin 20 are stitched.

The sanitary napkin 20 has a perimeter generally comprising longitudinal perimeter segments 32 and transverse perimeter segments 34. The perimeter defines the outer boundary of the sanitary napkin 20, while the longitudinal perimeter segments 32 and the transverse perimeter segments 34 define the outer boundary of the sanitary napkin 20 along each longitudinal side and each transverse end respectively.

Figure 2:
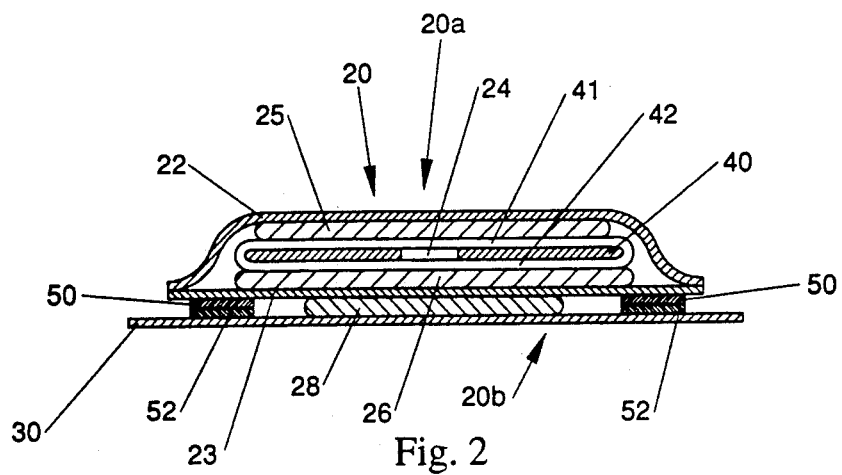
FIG. 2 is a cross-sectional view of the sanitary napkin of FIG. 1 taken along section line 2—2.

FIG. 2 is a cross-sectional view of the sanitary napkin 20 taken along section line 2—2 of FIG. 1. As can be seen in FIG. 2 the sanitary napkin 20 includes an adhesive element 28. The adhesive element 28 is positioned on the outwardly oriented face of backsheet 23, and, in use, serves to affix the sanitary napkin 20 to the wearer's undergarments, thereby maintaining the sanitary napkin 20 in place against the wearer's body. The adhesive element 28 may take the form of a coating of adhesive which is in strips or any other suitable pattern. Preferably the backsheet 23 is coated uniformly with a layer of pressure sensitive hot melt adhesive such as NS34-2823 as manufactured by National Starch and Chemical of Bridgewater, N.J.

The sanitary napkin 20 preferably includes two discrete segments of elastic material 50 attached to the outwardly oriented face or the garment facing surface of the backsheet 23. Releasably secured to the two discrete segments of elastic material 50 are two discrete segments of restraint material 52. The restraint material 52 releasably secures the elastic material 50 in a substantially tensioned state until separation of the elastic material 50 from the restraint material 52, whereupon the tension in the elastic material 50 is released.

Figure 9:
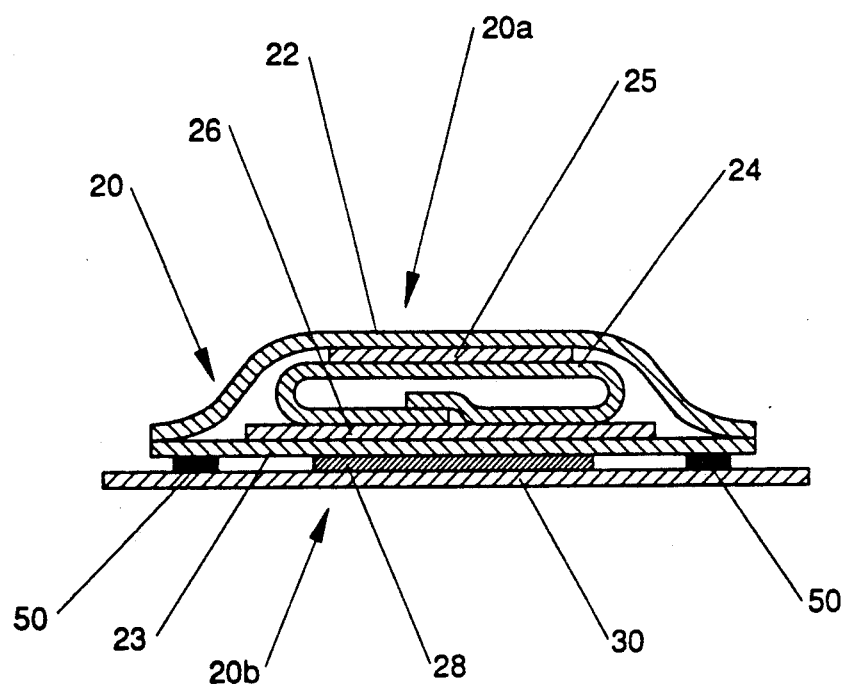
FIG. 9 is a cross-sectional view of another embodiment of a sanitary napkin of the present invention.

FIG. 9 is a cross-sectional view of another embodiment of a sanitary napkin 20 of the present invention. As can be seen in FIG. 9 sanitary napkin 20 preferably comprises a liquid pervious topsheet 22, a liquid impervious backsheet 23 joined with the topsheet 22, and an absorbent core 24 positioned between the topsheet 22 and backsheet 23. The sanitary napkin 20 also includes an acquisition layer 25 positioned generally between the topsheet 22 and the absorbent core 24. The sanitary napkin 20 also includes a nonwoven layer 26 positioned between the absorbent core 24 and the backsheet 23. The sanitary napkin 20 also includes an adhesive element 28 positioned on the outwardly oriented face of the backsheet 23. A wrapper 30 is releasably affixed to the adhesive element 28.

The sanitary napkin 20 preferably includes two discrete segments of elastic material 50 permanently attached to the outwardly oriented face or the garment facing surface of the backsheet 23. The wrapper 30 is preferably releasably secured to the two discrete segments of elastic material 50. The wrapper 30 preferably maintains the elastic material 50 in a substantially tensioned state until separation of the wrapper 30 from the elastic material 50, whereupon the tension in the elastic material 50 is released.

Figure 10:
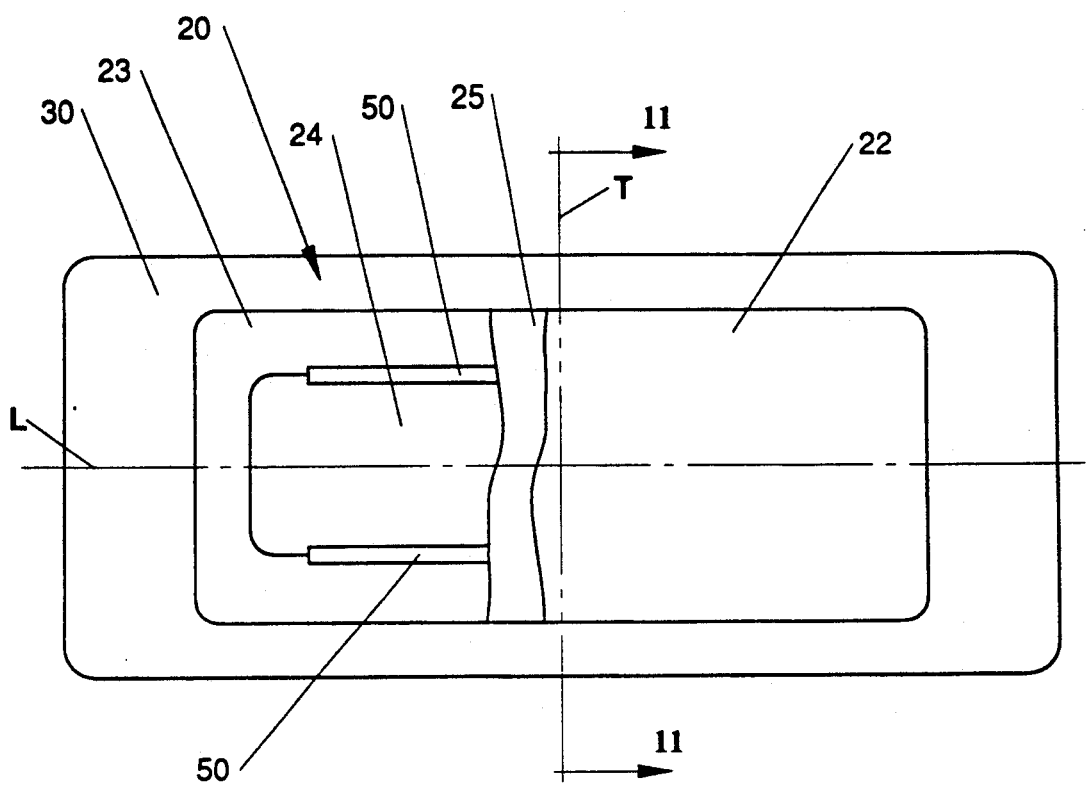
FIG. 10 is a top plan view of another embodiment of a sanitary napkin of the present invention.

FIG. 10 is a top plan view of another embodiment of a sanitary napkin 20 and a wrapper 30 of the present invention in its flat state with portions of the structure being cut-away to more clearly show the construction of the sanitary napkin 20 and with the portion of the sanitary napkin 20 which faces or contacts the wearer 20a, oriented towards the viewer. As shown in FIG. 10, the sanitary napkin 20 preferably comprises a liquid pervious topsheet 22, a liquid impervious backsheet 23 joined with the topsheet 22, and an absorbent core 24 positioned between the topsheet 22 and the backsheet 23. The sanitary napkin 20 also includes an acquisition layer 25 positioned generally between the topsheet 22 and the absorbent core 24. The sanitary napkin 20 preferably includes two discrete segments of elastic material 50 attached to the body facing surface of the backsheet 23 and to the longitudinal segments of the absorbent core 24.

Figure 11:
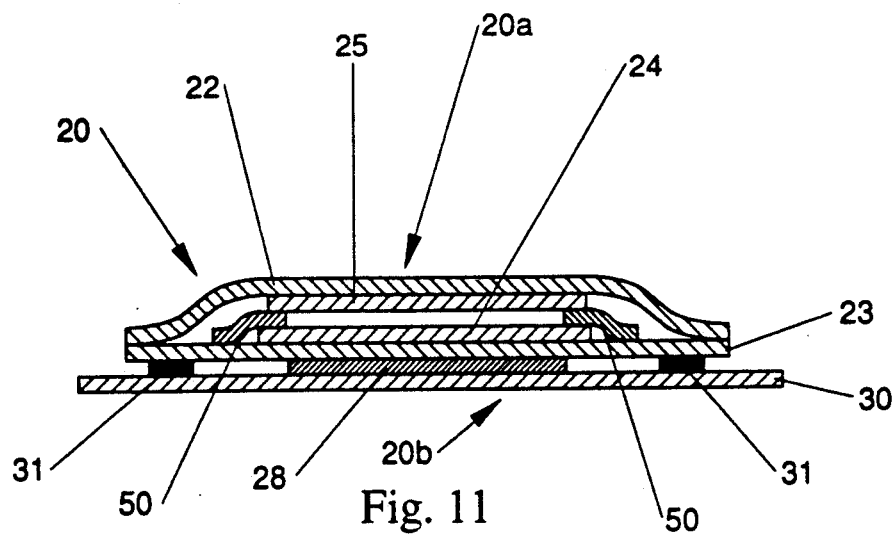
FIG. 11 is a cross-sectional view of the sanitary napkin of FIG. 10 taken along section line 11—11.

FIG. 11 is a cross-section view of the sanitary 20 taken along section line 11—11 of FIG. 10. As can be seen in FIG. 11 the sanitary napkin 20 includes an adhesive element 28 positioned on the garment facing surface of the backsheet 23.

The wrapper 30, which is releasably affixed to the outer or garment facing surface of the backsheet 23 maintains the elastic material 50 in a substantially tensioned state until separation of the wrapper 30 from the backsheet 23, whereupon the tension in the elastic material 50 is released. Preferably, the wrapper 30 includes stiffening members 31 on its inwardly oriented faces. Stiffening members 31 provide the wrapper 30 with additional support to maintain the elastic material 50 in a substantially tensional state until separation of the wrapper 30 from the backsheet 23.

Figure 12:
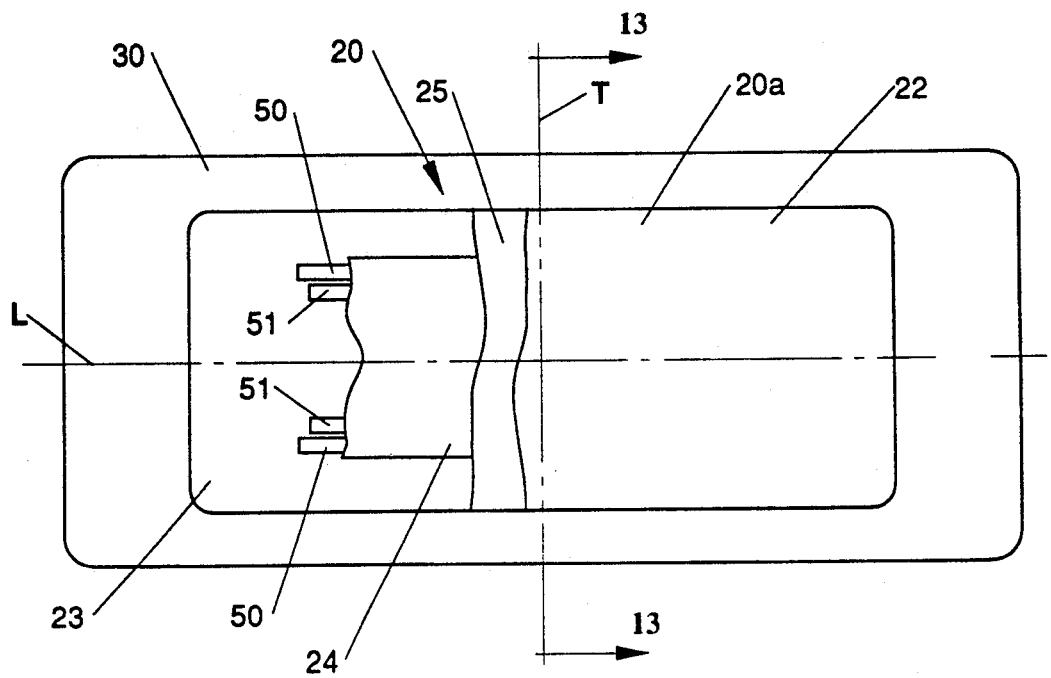
FIG. 12 is a top plan view of another embodiment of a sanitary napkin of the present invention.

FIG. 12 is a top plan view of an alternative embodiment of a sanitary napkin 20 and a wrapper 30 of the present invention in its flat-out state with portions of the structure being cut-away to more clearly show the construction of the sanitary napkin 20 and with the portion of the sanitary napkin 20 which faces or contacts the wearer 20a oriented towards the viewer. As shown in FIG. 12, the sanitary napkin 20 preferably comprises a liquid pervious topsheet 22, a liquid impervious backsheet 23 joined with the topsheet 22, and an absorbent core 24 positioned between the topsheet 22 and the backsheet 23. The sanitary napkin 20 also includes an acquisition layer 25 positioned generally between the topsheet 22 and the absorbent core 24. The sanitary napkin 20 preferably includes two discrete segments of elastic material 50 attached to the body facing surface of the backsheet 23. In addition, the sanitary napkin 20 preferably includes two additional discrete segments of elastic material 51 also attached to the body facing surface of the backsheet 23.

Figure 13:
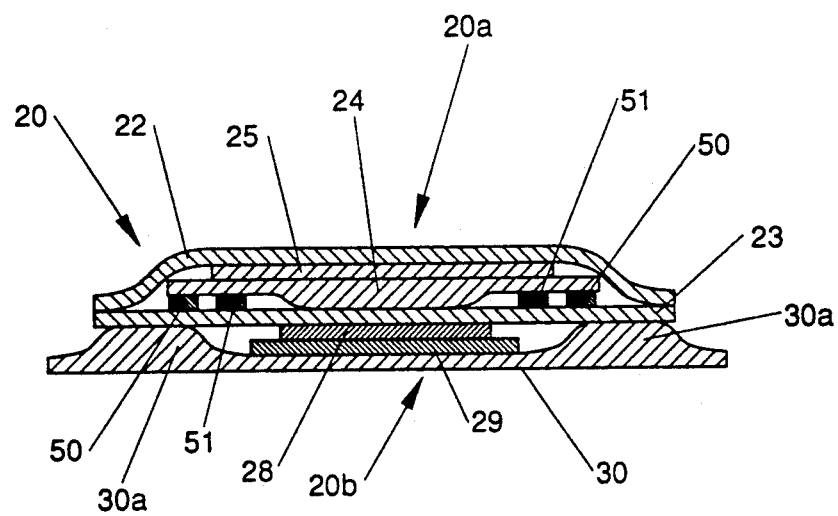
FIG. 13 is cross-sectional view of the sanitary napkin of FIG. 12 taken along section line 13—13.

FIG. 13 is cross-sectional view of the sanitary napkin 20 taken along section line 13—13 of FIG. 12. As can be seen in FIG. 13 the sanitary napkin 20 includes an adhesive element 28. The adhesive element 28 is positioned on the outwardly oriented face of the backsheet 23, and, in use, serves to affix the sanitary napkin 20 to the wearer's undergarments, thereby maintaining the sanitary 20 in place against the wearer's body. A release paper 29 is preferably positioned between the backsheet 23 and the wrapper 30.

The wrapper 30 maintains the discrete segments of the elastic material, 50 and 51, in a substantially tensioned state until separation of the wrapper 30 from the backsheet 23, whereupon the tension in the elastic material, 50 and 51, is released. Preferably, the wrapper 30 includes stiffening portions 30a. Stiffening portions 30a are thick portions of wrapper material which provide the additional support to maintain the elastic material, 50 and 51, is a substantially tensioned state until separation of the wrapper 30 from the backsheet 23.

The individual components of the sanitary napkin will now be looked at in greater detail.

2. Individual Components of the Sanitary Napkin

A. The Topsheet

The topsheet 22 is compliant, soft feeling, and non-irritating to the wearer's skin. Further, the topsheet 22 is liquid pervious permitting liquids (e.g., menses and/or urine) to readily penetrate through its thickness. A suitable topsheet 22 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

A preferred topsheet 22 comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, issued to Thompson on Dec. 30, 1975; U.S. Pat. No. 4,324,246, issued to Mullane et al. on Apr. 13, 1982; U.S. Pat. 4,342,314, issued to Radel et al. on Aug. 3, 1982; U.S. Pat. No. 4,463,045, issued to Ahr et al. on Jul. 31, 1984; U.S. Pat. No. 4,629,643, issued to Curro et al. on Dec. 16, 1986; and U.S. Pat. No. 5,006,394, issued to Baird on Apr. 9, 1991. Each of these patents are incorporated herein by reference. The preferred topsheet 22 for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet 22 is hydrophilic so as to help liquid to transfer through the topsheet 22 faster than if the body surface was not hydrophilic. This will diminish the likelihood that menstrual fluid will flow off the topsheet 22 rather than flowing into and being absorbed by the absorbent core 24. In a preferred embodiment, surfactant is incorporated into the polymeric materials of the formed film topsheet 22 such as is described in U.S. patent application Ser. No. 07/794,745, entitled "Absorbent Article Having A Nonwoven and Apertured Film Coversheet" filed on Nov. 19, 1991 by Aziz et al. Alternatively, the body surface of the topsheet 22 can be made hydrophilic by treating it with a surfactant such as is described in U.S. Pat. No. 4,950,264 issued to Osborn on Aug. 21, 1991 and U.S. Pat. No. 5,009,653, issued to Osborn on Apr. 23, 1991 both of which are incorporated herein by reference.

B. The Absorbent Core

The absorbent core 24 may be any absorbent means which is capable of absorbing or retaining liquids (e.g., menses and/or urine). As shown in FIG. 2, the absorbent core 24 has a body surface, a garment surface, side edges, and end edges. The absorbent core 24 may be manufactured in wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. An example of other suitable absorbent materials include creped cellulose wadding; meltblown polymers including coform; chemically stiffened, modified or cross-linked cellulosic fibers; capillary channel fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core 24 may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 24 should, however, be compatible with the design loading and the intended use of the sanitary napkin 20. Further, the size and absorbent capacity of the absorbent core 24 may be varied to accommodate different uses such as incontinence pads, pantiliners, regular sanitary napkins, or overnight sanitary napkins.

Exemplary absorbent structures for use as the absorbent core 24 of the present invention are described in U.S. Pat. 4,950,264, issued to Osborn on Aug. 21, 1990; U.S. Pat. No. 4,610,678, issued to Weisman et al. on Sep. 9, 1986; U.S. Pat. No. 4,834,735, issued to Alemany et al. on May 30, 1989; U.S. Pat. No. 5,009,653, issued to Osborne on Apr. 23, 1991; and European Patent Application No. 0 198 683, The Procter & Gamble Company, published Oct. 22, 1986 in the name of Duenk et al. Each of these patents are incorporated herein by reference.

A preferred embodiment of the absorbent core 24 comprises the laminate structure shown in FIG. 2. The laminate is comprised of a layer of superabsorbent polymeric (or absorbent gelling material) and one or more sheets or webs of cross-linked cellulosic fibers. Suitable cross-linked cellulosic fibers for the absorbent core 24 are described in U.S. Pat. No. 4,888,093 issued to Cook et al. on Dec. 19, 1989; U.S. Pat. No. 4,822,543, issued to Dean et al. on Apr. 18, 1989; U.S. Pat. No. 4,889,595, issued to Schoggen et al. on Dec. 26, 1989; and U.S. Pat. No. 4,898,642, issued to Moore et al. on Feb. 6, 1990; U.S. Pat. No. 4,935,022, issued Jun. 19, 1990 to Lash et al.; EPO Patent Application Publication Nos. 0 427 316 A2 and 0 427 317 A2 published in the name of Herron et al. on May 15, 1991; and EPO Patent Application Publication No. 0 429 112 A2 published in the name of Herron et al. on May 29, 1991 incorporated herein by reference.

The cross-linked cellulosic fibers in the embodiment shown in FIG. 2 comprises a single sheet that wraps the layers of particles of absorbent gelling material 40. The sheet is wrapped so that it appears as having a "c" configuration when viewed from the end. The wrapped sheet forms an upper layer 41 and a lower layer 42. In alternative embodiments, the laminate can be formed in many other manners, such as by providing separate webs of cross-linked cellulosic material (or other absorbent material) for the different layers of the absorbent core laminate other than a single sheet, or by providing it with additional layers.

In this type of core, curled, twisted, preferably chemically stiffened and cross-linked, cellulose fibers are refined to provide fibers which can be used in sheet form as the absorbent core. The preparation of suitable curled, chemically stiffened cellulosic fibers from which one can prepare the refined, curled, chemical stiffened cellulosic fibers used in detail in U.S. Pat. Nos. 4,888,903; 4,822,543; 4,889,595; 4,889,597; 4,889,596; and 4,898,642.

The use of such fibers in combination with absorbent gelling materials, and means for manufacturing such combinations, are described in U.S. Pat. No. 4,935,022. Such preparations typically involve the use of aldehydes, such as glutaraldehyde, as crosslinking agents. In addition, polycarboxylic acids can be used as crosslinking agents. It will be appreciated that other means for preparing other crosslinked cellulosic fibers are also known, and such fibers may also be used herein, although the fluid absorbency properties may be suboptimal as compared with the above-mentioned fibers. Reference can be made to the various citations in U.S. Pat. No. 4,898,642 and PCT U.S. Ser. No. 89 01581 for other fiber types. Once in hand, the curled cellulosic fibers are refined to provide the fibers used to prepare the preferred absorbent cores used in the practice of this invention.

C. Backsheet

The backsheet 23 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 23 prevents the exudates absorbed and contained in the absorbent core 24 from wetting articles which contact the sanitary napkin 20 such as pants, pajamas and undergarments. The backsheet 23 may thus comprise a woven or nonwoven material, polymeric films such as thermoplastic films of polyethylene or polypropylene, or composite materials such as a film-coated nonwoven material. Preferably, the backsheet 23 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet 23 is preferably embossed and/or matte finished to provide a more clothlike appearance. Further, the backsheet 23 may permit vapors to escape from the absorbent core 24 (i.e., breathable) while still preventing exudates from passing through the backsheet 23.

D. The Wrapper

A wrapper 30 is associated with, and has dimensions generally larger than those of the sanitary napkin 20. Thus, the wrapper 30 has longitudinal flap portions 36 comprising that portion of the wrapper 30 between the longitudinal edges 35 of the wrapper 30 and the longitudinal perimeter segments 32 of the sanitary napkin 20. In the preferred embodiment illustrated in FIG. 1, the wrapper 30 also has transverse flap portions 38 comprising that portion of the wrapper 30 between the transverse edges 37 of the wrapper 30 and transverse segments 34 of the sanitary napkin 20.

The wrapper 30 has opposed faces. One face is an inwardly oriented face which is oriented towards the adhesive 28 and the outwardly oriented face of the backsheet 23. The other face is an outwardly oriented face opposed to the inwardly oriented face and which is oriented away from the sanitary napkin 20. Preferably, the inwardly oriented face is release coated, to facilitate easy and convenient release of the wrapper 30 from the adhesive 28 on backsheet 23. In other words, the wrapper 30 is releasably affixed to the adhesive element 28. As used herein, "releasably affixed" refers to the condition of two or more components which may be attached and separated without destruction or undue distortion of either component. As discussed earlier herein, the adhesive 28 serves to affix the sanitary napkin 20 to the wearer's undergarments, thereby maintaining the sanitary napkin 20 in place against the wearer's body. The wrapper 30 protects the adhesive 28 from contamination or from sticking to areas other than those desired prior to use.

Silicon releases, as are well known in the art, have been found to work well. The wrapper 30 may be zone coated with the release coating only in the areas of the adhesive 28, or may be entirely release coated throughout the inwardly oriented face as desired. The wrapper 30 may be manufactured from films, paper, or other materials as are well known in the art. Preferably, the wrapper 30 is a polyethylene film having a thickness of from about 0.012 mm (0.5 mil) to about 0.12 mm (5.0 mil).

The wrapper 30 overlays the outwardly oriented face of backsheet portion 23 with the longitudinal flap portions 36 extending beyond the longitudinal perimeter segments 32. It is important to note that the wrapper 30 is not folded onto or otherwise brought into contact with the topsheet portion 22 while sanitary napkin 20 is in a substantially flat configuration as shown in FIG. 1. In other words, the inwardly oriented face of the wrapper 30 facing the backsheet portion 23 is in face to face relation with the backsheet portion only. However, upon folding of the wrapper 30 and sanitary napkin 20, the wrapper 30 will come into contact with portions of the topsheet 22.

An example of a suitable wrapper 30 is disclosed in commonly assigned U.S. Pat. No. 4,556,146 issued to Swanson et al. on Dec. 3, 1985, which patent is incorporated herein by reference.

Referring now to FIG. 11, the wrapper 30 preferably includes stiffening members 31 on its inwardly oriented face. The stiffening members 31 provide wrapper 30 with additional support in order to maintain the elastic material 50 in a substantially tensioned state until separation of the wrapper 30 from the backsheet 23. Preferably, the stiffening members 31 are made of polyethylene. Other suitable materials for stiffening members 31 include but are not limited to polyester, polyethylene terephthalate (PET), glycol modified PET copolymer (PETG) polystyrene, blends of polystyrene, polyetheylene laminated to paper, paper paperboard and cardboard.

As can be seen in FIG. 13 the wrapper 30 preferably includes stiffening portions 30a. Stiffening portions 30a are thick portions of wrapper material which provide the additional support needed to maintain the elastic material, 50 and 51, in a substantially tensioned state until separation of the wrapper 30 from the backsheet 23. Preferably the stiffening portions 30a are portions of wrapper material 30 which have been extruded at a thicker level than that of the remaining portions of the wrapper 30.

A sheet of release paper 29 is preferably positioned between the wrapper 30 and the backsheet 23. The release paper 29 is permanently secured to the inwardly oriented face of the wrapper 30 by an adhesive. The body facing surface of release paper 29 is release coated to facilitate easy and convenient release of the release paper 29 from the adhesive 28 on backsheet 23. That is, the release paper 29 is releasably affixed to the adhesive element 28.

E. The Adhesive Tab

Figure 7:
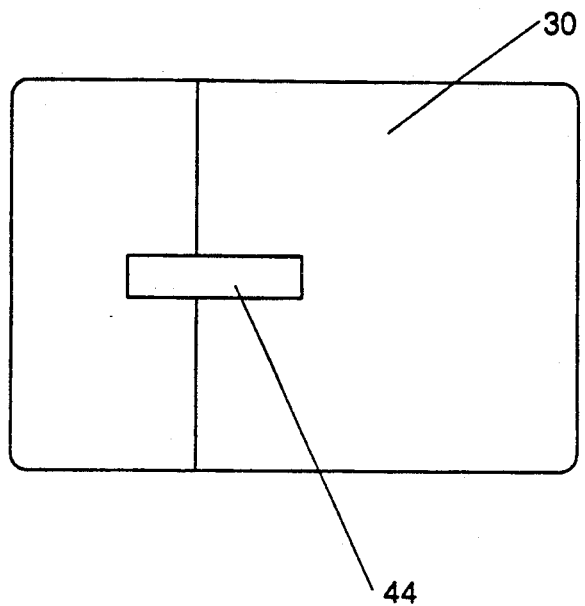
FIG. 7 is a perspective view of the sanitary napkin and its associated wrapper after they have been folded and sealed.
Figure 8:
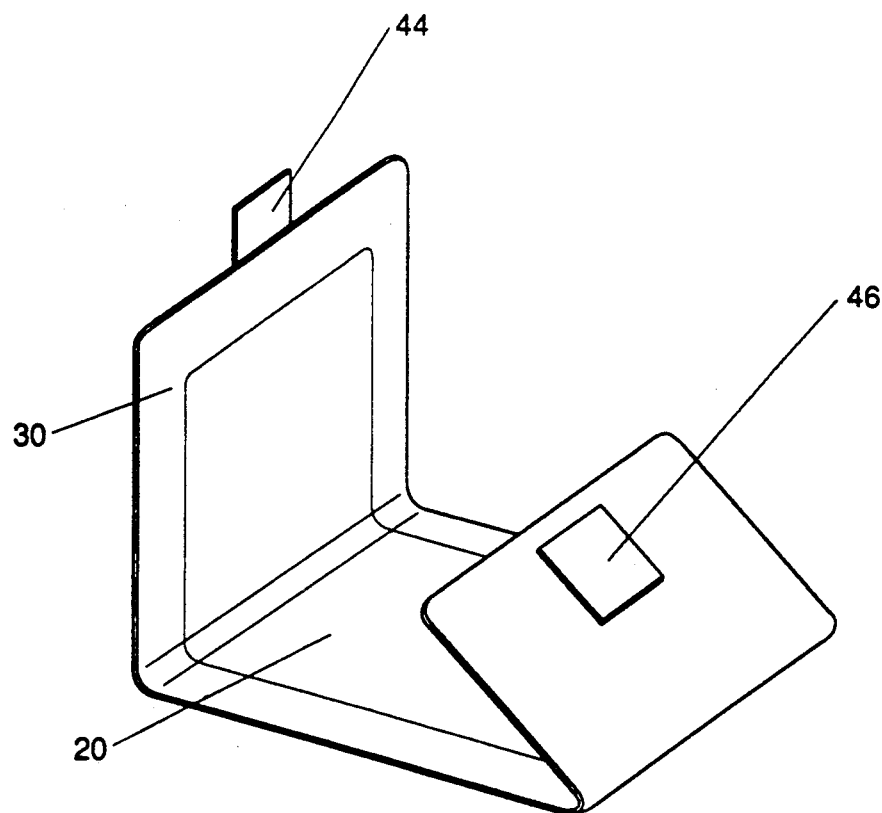
FIG. 8 is a perspective view of the sanitary napkin and its associated wrapper in a partially opened position.

As illustrated in FIGS. 7 and 8, a securement means is preferably provided on the outwardly oriented face of the wrapper 30. The securement means may be any means which will initially secure the package at the time of manufacture and maintain the package in a secured condition until it is opened by the consumer. In addition, the securement means will allow the user to reclose the package after use. An example of a suitable adhesive tab construction is disclosed in commonly assigned U.S. patent application entitled "Sanitary Napkin Wrapper and Adhesive Tab Construction for the Same", inventors Berg et al., Ser. No. 07/795,932 filed Nov. 15, 1991.

F. Elastic Material and Restraint Material

Figure 3:
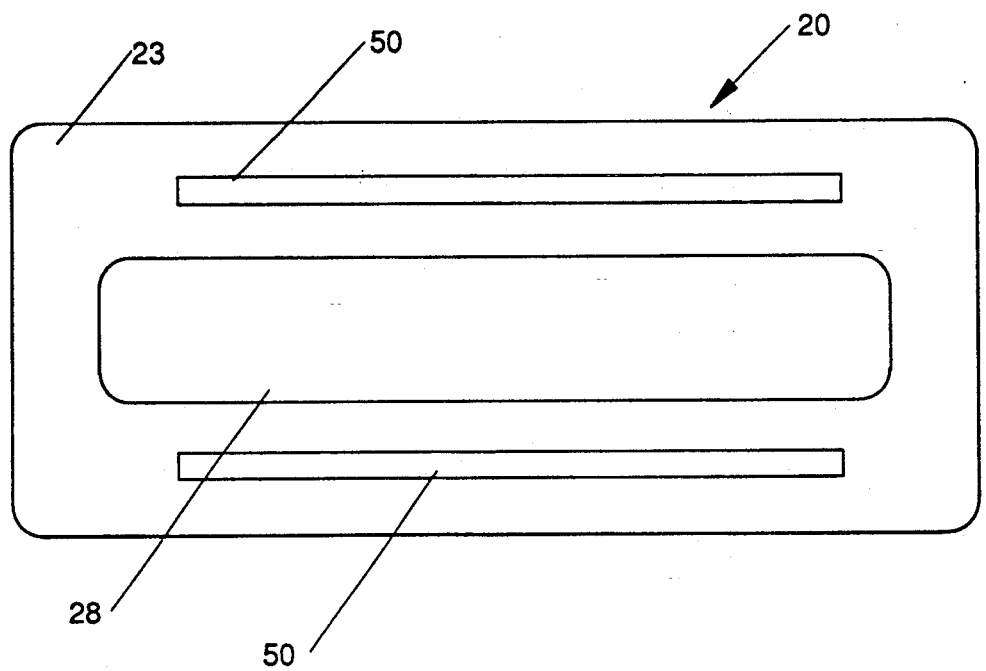
FIG. 3 is a plan view illustrating the preferred placement of the elastic material on the backsheet of the sanitary napkin.
Figure 4:
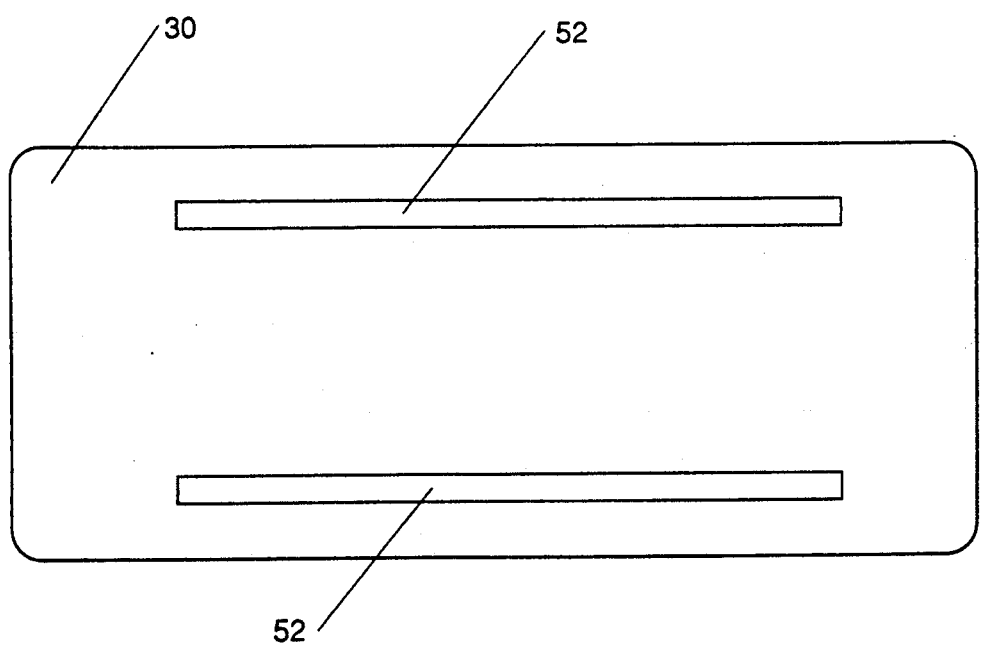
FIG. 4 is a plan view illustrating the preferred placement of the restraint material on the wrapper.

As illustrated in FIGS. 1 and 2, two discrete segments of an elastic material 50 are permanently secured to the exposed surface of backsheet portion 23 of the sanitary napkin 20. The preferred placement of the two segments of elastic material 50, substantially parallel to the longitudinal perimeter segments 32, is illustrated in FIG. 3. Releasably secured to the segments of elastic material 50 are two segments of restraint material 52. The two segments of restraint material 52 are permanently secured to the wrapper 30. The preferred placement of the two corresponding segments of restraint material 52, substantially parallel to the longitudinal edge 35 of the wrapper 30, is illustrated in FIG. 4.

The restraint material 52 releasably secures the elastic material 50 in a substantially tensioned state until separation of the elastic material 50 from the restraint material 52, whereupon the tension in the elastic material 50 is released.

While in the substantially tensioned state, the restraint material 52 and the elastic material 50 are substantially stable. The two materials can be machined, cut, and attached to other materials with little or no detrimental effect to the two materials. An example of a suitable restraint material 52 and elastic material 50 is disclosed in commonly assigned U.S. Pat. No. 4,908,247 issued to Baird et al. on Mar. 13, 1990 which patent is hereby incorporated herein by reference. Other suitable restraint materials include, but are not limited to, polyester, polyethylene terephthalate (PET), glycol modified PET copolymer (PETG), polystyrene, blends of polystyrene and polyethylene, polyethylene, polyethylene laminated to paper, and paper. Preferably, the elastic material 50 is a material that can undergo, moderate levels of reversible strain. Suitable elastic materials include, but are not limited to synthetic natural rubbers.

Figure 6:
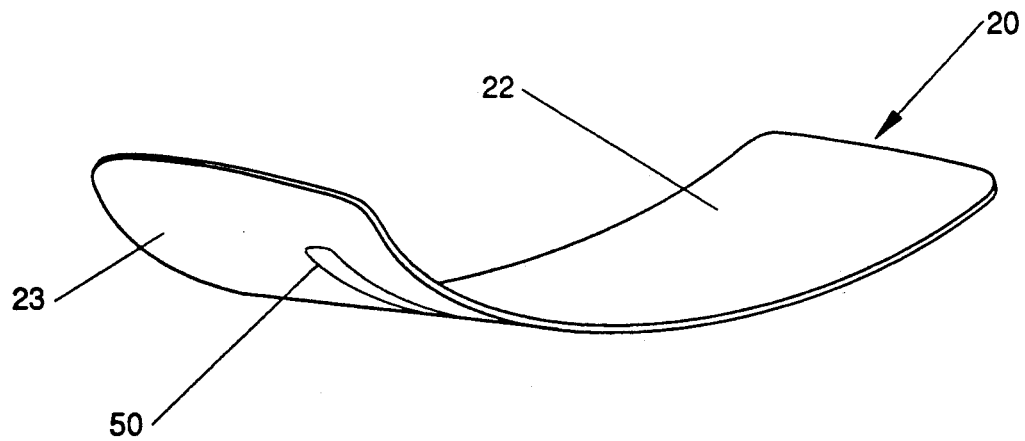
FIG. 6 is a perspective view of a sanitary napkin after its associated wrapper has been removed.

Upon separation of the restraint material 50 from the elastic material 50 the sanitary napkin 20 is in a substantially bistable state. In other words, upon separation and removal of the restraint material 52 from the elastic material 50, the sanitary napkin 20 may either form an upwardly cupped configuration or a downwardly cupped configuration under the shirring of the elastic material 50. The expected result is a downwardly cupped configuration as the elastic will naturally take the path of least resistance. However, by securing the elastic material 50 to the backsheet 23, the elastic material 50 is biased to shirr in one direction due to the direction of separation of the restraint material 52 from the elastic material 50. The separation of the restraint material 52 from the elastic material 50 releases the tension in the elastic material 50 causing the sanitary napkin 20 to become elasticized. As used herein the term "elasticized" refers to that condition where the restraint material is separated from the elastic material thereby releasing the tension in the elastic material. When the sanitary napkin 20 becomes elasticized upon the separation of the restraint material 52 from the elastic material 50, the sanitary napkin 20 forms an upwardly cupped configuration and elastically shirts in the direction of the tension release. This upwardly cupped configuration provides a sanitary napkin which more readily conforms to the contours of the user's body, as illustrated in FIG. 6.

The degree of upwardly cupping of the sanitary napkin 20 is determined by several factors, these include, but are not limited to, the location of the elastic material, the modulus of elasticity of the elastic material, the ability of the elastic material to maintain tension for extended periods of time, thickness of the elastic material, thickness of the sanitary napkin, stiffness of the sanitary napkin, length of the elastic material, and prestretch of the elastic material.

The length of the elastic material 50 applied to backsheet portion 23 can effect the degree of upward cupping. The longer the length of the elastic material 50 the greater the degree of upward cupping. In addition, as the amount of prestretch in the elastic material 50 is increased the degree or amount of cupping is also increased. Furthermore, the stiffness and/or thickness of the sanitary napkin 20 itself, or the materials which comprise sanitary napkin 20 can also effect the degree of cupping. In other words, as the thickness and/or stiffness of the sanitary napkin 20 increases, the amount or degree of upward cupping accordingly decreases. All of the above factors can be manipulated in conjunction with one another or independently to vary the degree and amount of cupping of the sanitary napkin 20 for particular uses as determined by the maker. For example, for a sanitary napkin 20 to be used during periods of heavy menstrual flow, it may be desirable to have a thick pad having a high degree of upward cupping. Therefore, since the thick pad will be relatively resistant to cupping, the tension, length, and/or selection of material for the elastic material 50 may be varied together or independently to get the desired degree of upward cupping on the thick pad.

FIG. 9 is a cross-sectional view of an alternative embodiment of a sanitary napkin 20 of the present invention. As can be seen in FIG. 9 the sanitary napkin 20 preferably comprises an elastic material 50 positioned between the wrapper 30 and the backsheet 23. The elastic material 50 is permanently secured to the exposed surface of the backsheet 23. The wrapper 30 is releasably affixed to the backsheet 23. In this embodiment, the wrapper 30 maintains the elastic material 50 in a substantially tensioned state until separation of the wrapper 30 from the elastic material 50 and the backsheet 23, whereupon the tension in the elastic material 50 is released. In order for the wrapper 30 to maintain the elastic material 50 in a substantially tensioned state until manual separation of the elastic material 50 from the wrapper 30, the wrapper 30 must be sufficiently strong to maintain the tensional forces in the elastic material 50. Suitable means for providing the wrapper 30 with sufficient strength include but are not limited to polyethylene laminated to paper, and paper. In addition, the wrapper 30 may include relatively thick portions at locations adjacent the elastic material 50. This may be accomplished by coextrusion or lamination of additional material in those isolated portions.

FIGS. 10 and 11 are illustrations of an alternative embodiment of a sanitary napkin 20 of the present invention. As can be seen in FIGS. 10 and 11, the sanitary napkin 20 preferably comprises two discrete segments of elastic material 50. Preferably the elastic material 50 is secured to the body facing surface of the backsheet 23 and also to the longitudinal segments of the absorbent core 24. In this embodiment, the wrapper 30 maintains the elastic material 50 in a substantially tensioned state until separation of the wrapper 30 from the backsheet 23, whereupon the tension in the elastic material 50 is released. As with the sanitary napkin illustrated in FIG. 9, the wrapper 30 must be sufficiently strong to maintain the elastic material 50 in a substantially tensioned state.

FIGS. 12 and 13 illustrate another embodiment of a sanitary napkin 20 of the present invention. As can be seen FIGS. 12 and 13, the sanitary napkin 20 preferably comprises a first elastic material 50 and second elastic material 51 positioned between the backsheet 23 and the absorbent core 24. The elastic materials 50 and 51 are permanently secured to the wearer or body facing surface of the backsheet 23. In this embodiment, the wrapper 30 maintains the elastic materials 50 and 51 in a substantially tensioned state until separation of the wrapper 30 from the backsheet 23, whereupon the tension in the elastic materials 50 and 51 is released. Again, the wrapper 30 must be of sufficient strength to maintain the elastic materials, 50 and 51, in a tensioned state.

While particular embodiments of the present invention have been illustrated and described, it will be apparent to those skilled in the art that various other embodiments can be carried out within the scope of the present invention. For example, elastic segments may be secured to the exterior surface of the backsheet, or placed in numerous positions between the backsheet and the topsheet of the sanitary napkin. The elastic may be a singular strand or multiple strands. In addition, the elastic segments may comprise one or more materials. The elastic segments may have varying thicknesses throughout their length, thus providing varying modulus of elasticity throughout the length of the elastic material. In addition, the elastic material may by positioned in any direction desired by the maker. For example, the elastic segments may run in a transverse direction across the sanitary napkin or in a diagonal direction. Transverse elastic segments will cause the sanitary napkin to have an inwardly cupped configuration upon the release of tension in the elastic material, i.e., separation of the wrapper from the backsheet.

It is important, however, that whatever embodiment is desired that the elastic material be maintained in a substantially restrained or tensioned state until separation of the wrapper from the sanitary napkin. By maintaining the elastic material in a substantially tensioned state, storage, packaging, and transport of the individually wrapped sanitary napkin will be greatly enhanced.

3. Use of the Sanitary Napkin

Figure 5:
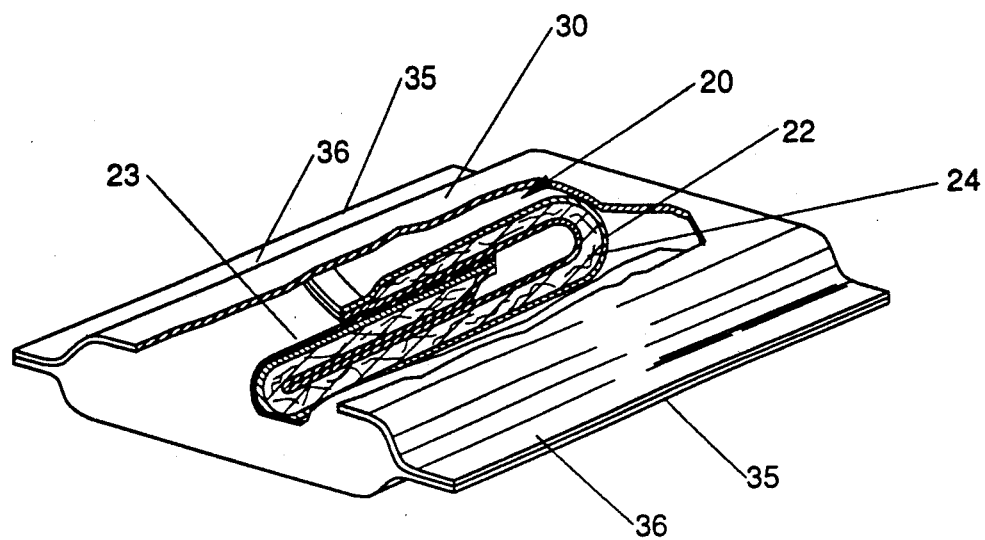
FIG. 5 is a partially cut-away perspective view of a sanitary napkin and its associated wrapper after they have been folded and sealed.

In use, an individually packaged sanitary napkin 20 as illustrated in FIG. 5 is provided to the user. The user first separates the adhesive tab 44 from complementary landing member 46. The user may then break the seal between the longitudinal flap portions 32 and unfold the sanitary napkin 20 and wrapper 30 combination. The user thereafter removes the wrapper 30 from the sanitary napkin 20, thereby releasing the tension in the elastic material 50. The release of tension in the elastic material 50 causes the sanitary napkin 20 to have a generally upwardly cupped shape due to the shirring of elastic material 50, as shown in FIG. 4. The sanitary napkin 20 may then be used as such devices normally are.

After use, the user can place the backsheet 23 of the sanitary napkin 20 on wrapper 30. The wrapper and pad can be folded or rolled together. Then the user can stick the adhesive tab 44 to a portion of the wrapper 30 other than complementary landing portion 46.

4. Method of Making the Sanitary Napkin of the Present Invention

Figure 14:
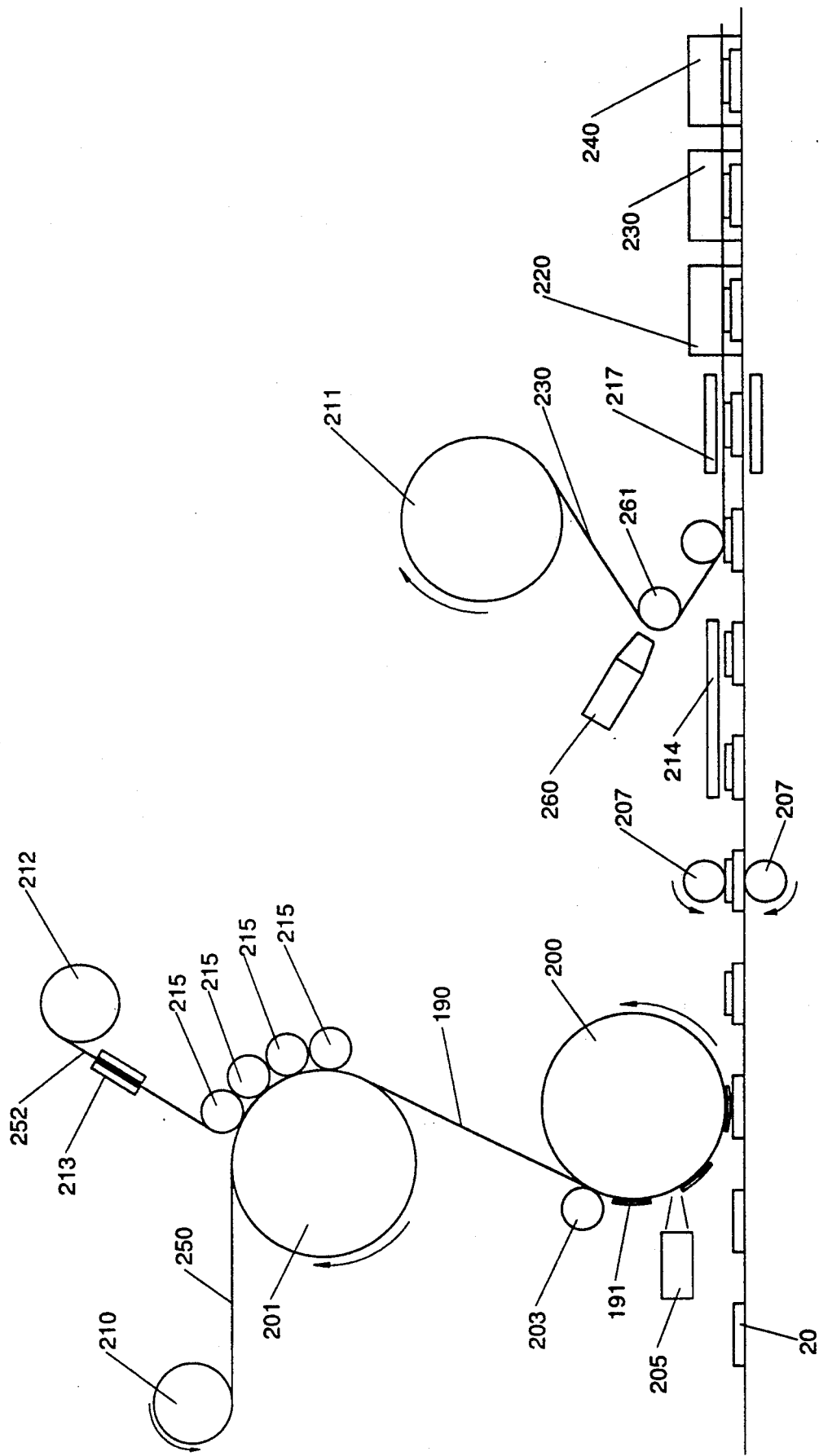
FIG. 14 is a simplified sectional side elevation view showing the assembly of sanitary napkins of the present invention.

Referring to FIG. 14 there is shown a simplified sectional side elevation view illustrating the assembly of the sanitary napkin illustrated in FIGS. 1 and 2 having tensioned elastic material secured thereto. The sanitary napkin 20 which includes a liquid pervious topsheet 22, a liquid impervious backsheet 23 joined with the topsheet 22 and an absorbent core 24 positioned between the topsheet 22 and the backsheet 23 is assembled by methods commonly known in the art. The sanitary napkin may also include an acquisition layer 25 positioned between the topsheet 22 and the absorbent core 24 and a nonwoven 27 positioned between the absorbent core 24 and the backsheets 23. The assembled sanitary napkins 20 are fed towards assembly station 200 with their backsheets 23 oriented towards the assembly station 200.

Above assembly 200 is a vacuum drum 201 for combining a continuous ribbon of elastic material 250 with a continuous ribbon of restraint material 252. The elastic material 250 is fed from feed roll 210 onto the vacuum drum 201. Speed differential between the elastic supply feed roll 210 and the vacuum drum 201 is used to control the desired prestretch of elastic material 250 for the assembly process. The restraint material 252 is fed from feed roll 212 into heat tunnel 213 whereby the restraint 252 material is pre-heated. The heated restraint material 252 is then fed onto the vacuum drum 201. Combining rolls 215 around the periphery of vacuum drum 201 are heated or cooled as needed to obtain the proper process conditions. As the vacuum drum 201 rotates, the combining rolls 215 apply pressure to the elastic material 250 and restraint material 252 thereby mechanically securing the elastic material 250 to the restraint material 252 forming a continuous ribbon 190 of tensioned elastic material and restraint material. In an alternative embodiment, the continuous ribbon 190 of tensioned elastic material and restraint material can be made off-line.

The combined ribbon of elastic material and restraint material 190 is fed toward assembly station 200 on a feminine hygiene pad converting line using known assembly technology. This operation takes place after the sanitary napkin elements (topsheet, backsheet, and core) are assembled and prior to the placement of the sanitary napkin 20 onto the wrapper material. Knife 203 cuts the combined ribbon 190 into discrete lengths (approximately 4 inches long) and using cut and slip technology places one such cut segment on each side of the backsheet 23 of the sanitary napkin 20 along the longitudinal edge as shown in FIG. 3. These discrete lengths of restrained elastic material 191 are secured to the backsheet 23 of the sanitary napkin 20 by applying a coating of hot melt adhesive at glue applicator 205 to the elastic side of the restrained elastic material prior to placement on the sanitary napkin 20. The sanitary napkin 20 assembly is then fed between a set of special nip rolls 207 to both set the hot melt in place and to help cool the hot adhesive.

The next step in the assembly process of this preferred embodiment is to combine the sanitary napkin 20 assembly with the continuous web of wrapper material 230. This is accomplished by combining a continuous web of polyethylene film 230 from feed roll 211 (approximately one mill) to the stream of sanitary napkin 20 assemblies as they continue through the converting line. A panty fastening adhesive (PFA) is applied intermittently to web 230 at applicator 260. Chill roll 261 prevents undesirable distortion as the heated PFA is applied to web 230. The PFA is applied to the web 230 to later be transferred to the backsheet of the absorbent article to provide securement of the article to the undergarment during use. During this combining process a permanent bond must be made between the restraint material of the previously positioned restrained elastic material and the film wrapper material 230. This permanent bond is accomplished by applying a limited amount of heat at heater bar 214 to the restraint material side of the restrained elastic material prior to combining with the wrapper film 230. The combined assembly is then passed through a heated compression station 217 to permanently bond the restraint material to the wrapper film. This permanent bond is enhanced by having a laminate restraint material that has a top surface that contains a low temperature melt surface such as an EVA copolymer material.

The wrapper material 230 on the assembled sanitary napkin structure is then cut into discrete segments at station 220 and the sanitary napkin and wrapper assembly is rotated ninety degrees before being folded as a unit.

That is, they are folded together with the wrapper 30 remaining in place with respect to the sanitary napkin 20. Preferably, the sanitary napkin 20 is folded lengthwise into thirds about two fold-axes 60, as shown in FIG. 1. The longitudinal flap portions 36 are frangably sealed using any of the well-known sealing techniques at station 230. For example, the longitudinal flap portions 36 may be heat sealed, glued, ultrasonically bonded, or crimped or any combination thereof. The adhesive tab 44 with complementary landing member 46 is then secured to the exposed surface of the wrapper 30 at station 240. The folded and sealed sanitary napkin 20 with wrapper 30 is illustrated in FIG. 5.

There are many alternative assembly methods and individual unit operations that can be employed in the construction of the present invention. For example, the combined elastic and restraint material could be placed on the sanitary napkins one at a time or could be placed on the sanitary napkins simultaneously. The combined elastic and restraint material could be supplied in a non-continuous precut form and thus eliminate the on-line cutting operation. The combined elastic and restraint material glue mounting operations could be located such that the glue were placed directly on the sanitary napkin rather than on the combined elastic and restraint material. This glue operation could also be eliminated if the combined elastic and restraint material were mounted with the use of a pressure sensitive glue or other standard mounting means. The means by which the permanent bond of the restraint portion of the combined elastic and restraint material to the wrapper film is accomplished can also incorporate the use of hot melt glue or other known permanent bonding techniques. If the finished product is to contain a panty fastening adhesive (PFA), this material can be applied to the sanitary napkin prior to the application of the combined elastic and restraint material during any part of the application process or it can be applied directly to the wrapper material so as to transfer to the sanitary napkin when it is combined with the sanitary napkin.

Figure 15:
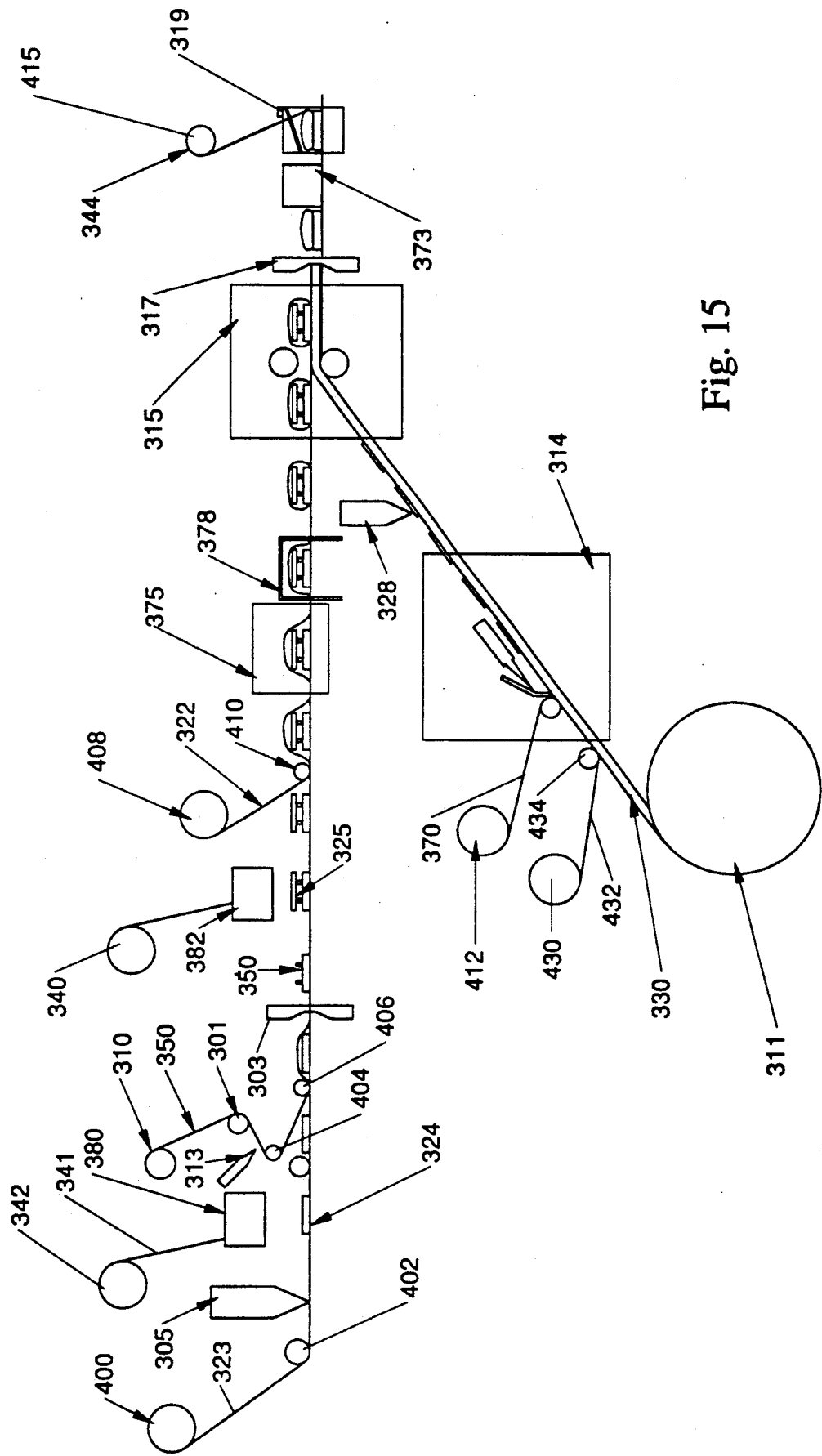
FIG. 15 is a simplified sectional scale elevation view showing the assembly of sanitary napkins of the present invention.

Referring now to FIG. 15 there is shown a simplified sectional side elevation view illustrating the assembly of sanitary napkins of FIGS. 10-13 of the present invention. A web of backsheet material 323 is fed from roll 400 to nip rolls 402. A hot melt adhesive is applied to backsheet material 323 at station 305. An absorbent core 324 is then fed onto backsheet web 323 at absorbent core assembly station 380. The core material 341 is fed from the core supply roll 342, positioned above core assembly station 380, to the core assembly station 380. A continuous ribbon of elastic material 350 is fed from feed roll 310 to roller 301. Prior to reaching the web of backsheet material 323 an adhesive is applied at adhesive applicator 313 to the elastic ribbon 350. After adhesive is applied to elastic ribbon 350, it is fed to rolls 404 and 406. The speed differential between feed roll 310 and roll 301 controls the desired prestretch for the elastic ribbon 350. The elastic ribbon 350 is intermittently glued to the backsheet material 323. The elastic material may also be glued to the absorbent core 324. A knife 303 severs or cuts the ends of the continuous elastic ribbon 350 thereby providing discrete segments. An acquisition layer 325 is then placed upon the absorbent core 324 directly below acquisition layer assembly station 382. Directly above acquisition layer assembly station 382 is an acquisition layer feed roll 340 which feeds acquisition material 343 to assembly station 382. A continuous ribbon of topsheet material 322 is fed from roll 408 toward roller 410. The topsheet material 322 is then secured to the backsheet material 323 at station 375. The sanitary napkin is cut into its final shape by cutter 378. The sanitary napkin is then fed to assembly station 315.

Simultaneously, a continuous web of wrapper material 330 is fed from roll 311 to assembly station 314. A continuous ribbon of stiffening material 370 is fed from roll 412 towards assembly station 314. The stiffening material 370 is secured to the continuous wrapper material 330 at station 314. A layer of release coating is applied to the wrapper material 330 at station 328. The wrapper assembly is then fed toward combining station 315.

In an alternative embodiment, a continuous web of release paper 432 is fed from roll 430 to station 434. At station 434 the web of release paper 432 is intermittently applied to the web of wrapper material 330. Preferably, PFA may be applied intermittently to the release paper 432 prior to reaching station 434.

At combining station 315 the sanitary napkin is then attached to the wrapper material 330. A vacuum maintains the elastic material in a substantially tensioned state until the wrapper is attached to the backsheet. A knife 317 cuts the wrapper material into discrete segments. At station 373 a folding crimping operation of the wrapper sanitary napkin assembly occurs. A continuous roll of releasable tape 344 is fed from roll 415 and is attached to the outer surface of the folded individually wrapped package at station 319.

By maintaining the sanitary napkin 20 in a substantially flat configuration, the sanitary napkin 20 may be packaged, transported, shipped, and handled in a more convenient less bulky manner as compared to one having a curved configuration as in prior art sanitary napkins which have one or more elastic members located within the sanitary napkin itself.

While particular embodiments of the present invention have been illustrated and described, modification may be made to the sanitary napkin without departing from the spirit and scope of the present invention. Accordingly, the present invention comprises all embodiments within the scope of the appended claims.

What is claimed is:

1. An individually wrapped disposable absorbent article comprising:
   (a) an absorbent core having a first surface and a second surface;
   (b) a fluid permeable topsheet secured in overlaying relation to said first surface of said absorbent core;
   (c) a fluid impermeable backsheet secured in overlaying relation to said second surface of said absorbent core, said backsheet having an exposed surface and an inwardly oriented surface, said exposed surface of said backsheet including a layer of adhesive;
   (d) a wrapper for covering the layer of adhesive on the exposed surface of said backsheet, said wrapper having an exposed surface and an inwardly oriented surface, said inwardly oriented surface of said wrapper being releasably affixed to the exposed surface of said backsheet by said layer of adhesive; and
   (e) an elastic material secured to said backsheet, said elastic material being held in tension while said wrapper is affixed to said backsheet, a substantial portion of said absorbent article being maintained in a planar configuration while said wrapper is affixed to said backsheet, separation of said wrapper from said backsheet releasing the tension in said elastic material causing said absorbent article to form an upwardly cupped configuration.

2. The disposable absorbent article according to claim 1 wherein said elastic material is secured to the exposed surface of said backsheet.

3. The disposable absorbent article according to claim 2 further comprising a restraint material being releasably secured in fixed relation to said elastic material, said restraint material maintaining said elastic material in a substantially tensioned state until separation of said wrapper from said backsheet.

4. The disposable absorbent article according to claim 2 further comprising stiffening members secured to the inwardly oriented surface of said wrapper.

5. The disposable absorbent article according to claim 1 wherein said elastic material is secured to the inwardly oriented surface of said backsheet.

6. The disposable absorbent article according to claim 5 wherein said elastic material is secured to said absorbent core.

7. The disposable absorbent article according to claim 5 further comprising stiffening members secured to the inwardly oriented surface of said wrapper.

8. The disposable absorbent article according to claim 1 further comprising an adhesive tab secured to the exposed surface of said wrapper for maintaining said disposable absorbent article in a secured condition until opening.

9. The disposable absorbent article according to claim 1 further comprising a release paper positioned between said wrapper and said backsheet.

10. The disposable absorbent article according to claim 1 wherein said disposable absorbent article is a catamenial pad.

11. An individually wrapped disposable absorbent article comprising:
   (a) an absorbent core having a first surface and a second surface;
   (b) a fluid permeable topsheet secured in overlaying relation to said first surface of said absorbent core;
   (c) a fluid impermeable backsheet secured in overlaying relation to said second surface of said absorbent core, said backsheet having an exposed surface and an inwardly oriented surface, said exposed surface of said backsheet including a layer of adhesive;
   (d) a wrapper for covering the layer of adhesive on the exposed surface of said backsheet, said wrapper having an exposed surface and an inwardly oriented surface, said inwardly oriented surface of said wrapper being releasably affixed to said backsheet, separation of said wrapper from said backsheet releasing the tension in said elastic member causing said disposable absorbent article to form an upwardly cupped configuration.

12. The disposable absorbent article according to claim 11 further comprising a restraint material being releasably secured in fixed relation to said elastic material, said restraint material maintaining said elastic material in a substantially tensioned state until separation of said wrapper from said backsheet.

13. The disposable absorbent article according to claim 11 further comprising stiffening members secured to the inwardly oriented face of said wrapper.

14. The disposable absorbent article according to claim 1 wherein said article is a catamenial pad.

15. The disposable absorbent article according to claim 11 further comprising an adhesive tab secured to the exposed surface of said wrapper for maintaining said disposable absorbent article in a secured condition until opening.

16. The disposable absorbent article according to claim 15 further comprising a cooperating landing member secured to the exposed surface of said wrapper.

17. An individually wrapped disposable absorbent article comprising:
   (a) an absorbent core having a first surface and a second surface;
   (b) a fluid permeable topsheet secured in overlaying relation to said first surface of said absorbent core;
   (c) a fluid impermeable backsheet secured in overlaying relation to said second surface of said absorbent core, said backsheet having an exposed surface and an inwardly oriented surface, said exposed surface of said backsheet including a layer of adhesive;
   (d) a wrapper for covering the layer of adhesive on the exposed surface of said backsheet, said wrapper having an exposed surface and an inwardly oriented surface, said inwardly oriented surface of said wrapper being releasably affixed to said backsheet by said adhesive; and (e) an elastic material permanently secured to the inwardly oriented surface of said backsheet, said elastic material being held in tension while said wrapper is affixed to said backsheet, a substantial portion of said absorbent article being maintained in a planar configuration while said wrapper is affixed to said backsheet separation of said wrapper from said backsheet releasing the tension in said elastic material causing said disposable absorbent article to form an upwardly cupped configuration.

18. The disposable absorbent article according to claim 17 wherein said elastic material is secured to said absorbent core.

19. The disposable absorbent article according to claim 17 further comprising stiffening members secured to the inwardly oriented surface of said wrapper.

20. The disposable absorbent article according to claim 17 further comprising an adhesive tab secured to the exposed surface of said wrapper for maintaining said disposable absorbent article in a secured condition until opening.

21. The disposable absorbent article according to claim 17 wherein said article is a catamenial pad.

22. The disposable absorbent article according to claim 17 wherein said disposable absorbent article and said wrapper are folded as a unit about at least two fold-axes.

* * * * *

UNITED STATES PATENT AND TRADEMARK OFFICE
CERTIFICATE OF CORRECTION

PATENT NO. : 5,295,988

DATED : March 22, 1994

INVENTOR(S) : DELMAR R. MUCKENFUHS    KIM M. ROY

It is certified that error appears in the above-identified patent and that said Letters Patent is hereby corrected as shown below:

Column 12, line 21, "shirts" should read --shirrs--.

Column 18, line 29, Claim 11, after "sheet" the following should appear:

--by said adhesive; and (e)    an elastic material permanently secured to the exposed surface of said backsheet, said elastic material being held in tension while said wrapper is affixed to said backsheet, a substantial portion of said absorbent article being maintained in a planar configuration while said wrapper is affixed to said backsheet--

Column 18, line 43, Claim 14, "1" should be --11--.

Signed and Sealed this

Twenty-sixth Day of July, 1994

Attest:

*Attesting Officer*

BRUCE LEHMAN

*Commissioner of Patents and Trademarks*